(12) United States Patent
Chao et al.

(10) Patent No.: US 7,282,353 B2
(45) Date of Patent: Oct. 16, 2007

(54) PROTEIN ISOLATION

(75) Inventors: Yu-Chan Chao, Taipei (TW);
Tzu-Ching Lee, Taichung (TW)

(73) Assignee: Academia Sinica, Nan-Kang, Taipei (TW)

( * ) Notice: Subject to any disclaimer, the term of this patent is extended or adjusted under 35 U.S.C. 154(b) by 0 days.

(21) Appl. No.: 10/921,741

(22) Filed: Aug. 19, 2004

(65) Prior Publication Data

US 2005/0048075 A1    Mar. 3, 2005

Related U.S. Application Data

(60) Provisional application No. 60/496,161, filed on Aug. 19, 2003.

(51) Int. Cl.
*C12P 21/04* (2006.01)
(52) U.S. Cl. .................................................. 435/69.7
(58) Field of Classification Search ............. 435/235.1, 435/243, 320.1
See application file for complete search history.

(56) References Cited

U.S. PATENT DOCUMENTS 4,870,023 A * 9/1989 Fraser et al. ............. 435/235.1

5,976,552 A * 11/1999 Volvovitz ................ 424/199.1

OTHER PUBLICATIONS

Ikeda et al., Characterizations of natural and induced polyhedrin gene mutants of *Bombyx mori* cytoplasmic polyhedrosis viruses, Arch. Virol. (1998) 143: 241-248.*
GenCore version 5.1.6, Result 1, pp. 1-7.*
Verne A. Luckow et al. "Signals Important for High-Level Expression of Foreign Genes in *Autographs californica* Nuclear Polyhedrosis Virus Expression Vectors", Virology 167:56-71, 1988.
J. H. McLinden et al. "Expression of foreign epitopes on recombinant occlusion bodies of baculovirus". Vaccine 10(4):231-237, 1992.

* cited by examiner

*Primary Examiner*—Karen Cochrane Carlson
*Assistant Examiner*—Agnes B. Rooke
(74) *Attorney, Agent, or Firm*—Fish & Richardson P.C.

(57) ABSTRACT

A fusion protein containing a polyhedrin of a virus and a foreign polypeptide sequence. Also disclosed are a recombinant occlusion body containing the fusion protein, an isolated nucleic acid containing a sequence encoding the fusion protein, and a recombinant virus containing the nucleic acid. Within the scope of this invention are related expression vectors, host cells, compositions, and preparation methods.

28 Claims, No Drawings

PROTEIN ISOLATION

RELATED APPLICATION

This application claims priority to U.S. Provisional Application Ser. No. 60/496,161, filed on Aug. 19, 2003, the contents of which are incorporated by reference in their entirety.

BACKGROUND

Baculoviruses are a group of rod-shaped, enveloped, double-stranded DNA viruses having a circular, supercoiled genome varying from 90 to 160 kb in size. They have been successfully used for efficient expression of engineered proteins. A baculovirus system is more attractive than other protein expression systems because of its high level expression, posttranslational modification ability, and safety for use in humans (Smith et al., 1983, Mol. Cell Biol. 3, 2156-2165).

However, the yield of engineered protein prepared from a baculovirus system is not satisfactory. First, the peak time for engineered protein production varies from 2 to 6 days post infection (dpi) (Chatterji et al., 1996, Gene 171, 209-213; Liebman et al., 1999, Biotechniques 26, 36-42; and Pennock et al., 1984, Mol. Cell Biol. 4, 399-406). These variations may result from the concentrations of viruses applied, host cell numbers, virus infection conditions, and promoters used. As a baculovirus system is a lytic system, engineered proteins often leak upon maturation of viral progenies, leading to loss of the proteins. Although the maturation times of the progeny viruses are similar, secondary infection complicates the peak time. This is especially evident when lower multiplicity of infection (MOI) is used. Accordingly, protein yield is not satisfactory. Second, conventional protein recovery methods also entail loss of engineered proteins. Numerous techniques have been developed to improve the yield of engineered protein (Kennedy, 1990; Garcia & Pires, 1993, and Terpe, 2003). Nonetheless, they are either expensive or labor consuming.

Thus, there is a need for a baculovirus expression system and method for efficient protein isolation.

SUMMARY

This invention is based, at least in part, on the discovery that fusion proteins containing viral polyhedrin form occlusion bodies in a host cell and that the fusion proteins can be easily isolated from the host cell. Listed below are polyhedrin sequences of baculovirus and cytoplasmic polyhedrosis virus (CPV):

```
Baculovirus polyhedrin:            (SEQ ID NO: 1)
MPDYSYRPTIGRTYVYDNKYYKNLGAVIKNAKRKKH

FAEHEIEEATLDPLDNYLVAEDPFLGPGKNQKLTLF

KEIRNVKPDTMKLVVGWKGKEFYRETWTRFMEDSFP

IVNDQEVMDVFLVVNMRPTRPNRCYKFLAQHALRCD

PDYVPHDVIRIVEPSWVGSNNEYRTSLAKKGGGCPI

MNLHSEYTNSFEQFIDRVIWENFYKPIVYIGTDSAE

EEEILLEVSLVFKVKEFAPDAPLFTGPAY
```

```
CPV polyhedrin:                    (SEQ ID NO: 2)
MADVAGTSNRDFRGREQRLFNSEQYNYNNSLNGEVS

VWVYAYYSDGSVLVINKNSQYKVGISETFKALKEYR

EGQHNDSYDEYEVNQSIYYPNGGDARKFHSNAKPRA

IQIIFSPSVNVRTIKMAKGNAVSVPDEYLQRSHPWE

ATGIKYRKIKRDGEIVGYSHYFELPHEYNSISLAVS

GVHKNPSSYNVGSAHNVMDVFQSCDLALRFCNRYWA

ELELVNHYISPNAYPYLDINNHISYGVALSNRQ
```

One aspect of this invention features a fusion protein that contains (i) a polyhedrin sequence of a virus or its functional equivalent that is at least 70, e.g., 80, 100, 150, or 200, amino acids in length, and (ii) a foreign polypeptide sequence that is at least 10 amino acids in length. A plurality of the fusion proteins, in the absence of a wild type polyhedrin of the virus, form occlusion bodies in a host cell. The virus can be a baculovirus or a CPV. In one embodiment, the viral polyhedrin sequence contains SEQ ID NO: 1 or 2. In the fusion protein, the foreign polypeptide sequence can be 10-1,000, e.g., 100-500, amino acids in length. It can be any protein sequence of interest, such as a fluorescent proteins protein (GFP) or VP1 capsid protein of the foot and mouth disease virus. Listed below are their sequences:

```
GFP:                               (SEQ ID NO: 5)
MVSKQILKNTGLQEIMSFKVNLEGVVNNHVFTMEGC

GKGNILFGNQLVQIRVTKGAPLPFAFDILSPAFQYG

NRTFTKYPEDISDFFIQSFPAGFVYERTLRYEDGGL

VEIRSDINLIEEMFVYRVEYKGRNFPNDGPVMKKTI

TGLQPSFEVVYMNDGVLVGQVILVYRLNSGKFYSCH

MRTLMKSKGVVKDFPEYHFIQHRLEKTYVEDGGFVE

QHETAIAQLTSLGKPLGSLHEWV
```

```
VP1 protein:                       (SEQ ID NO: 7)
TTSAGESADPVTATVENYGGETQVQRRQDTDIAFIL

DRFVKVKPKEQVNVLDLMQIPAHTLVGALLRTATYY

FSDLELAVKHEGDLTWVPNGAPETALDNTTNPTAYH

KEPLTRLALPYTAPHRVLATVYNGSSKYGDTSTNNV

RGDLQVLAQKAERTLPTSFNFGAIKATRVTELLYRM

KRAETYCPRPLLAIQPSDARHKQRIVAPAKQLL
```

The invention also features an isolated nucleic acid containing a sequence that encodes the above-mentioned fusion protein. The nucleic acid can contain those encoding the above-mentioned baculovirus polyhedrin, CPV polyhedrin, GFP, or VP1 (e.g., SEQ ID NO: 3, 4, 6, or 8, listed below)

```
ATGCCGGATTATTCATACCGTCCCACCATCGGGCGTA   SEQ ID NO: 3

CCTACGTGTACGACAACAAGTACTACAAAAATTTAGG

TGCCGTTATCAAGAACGCTAAGCGCAAGAAGCACTTC

GCCGAACATGAGATCGAAGAGGCTACCCTCGACCCCC
```

-continued

TAGACAACTACCTAGTGGCTGAGGATCCTTTCCTGGG
ACCCGGCAAGAACCAAAAACTCACTCTCTTCAAGGAA
ATCCGTAATGTTAAACCCGACACGATGAAGCTTGTCG
TTGGATGGAAAGGAAAAGAGTTCTACAGGGAAACTTG
GACCCGCTTCATGGAAGACAGCTTCCCCATTGTTAAC
GACCAAGAAGTGATGGATGTTTTCCTTGTTGTCAACA
TGCGTCCCACTAGACCCAACCGTTGTTACAAATTCCT
GGCCCAACACGCTCTGCGTTGCGACCCCGACTATGTA
CCTCATGACGTGATTAGGATCGTCGAGCCTTCATGGG
TGGGCAGCAACAACGAGTACCGCATCAGCCTGGCTAA
GAAGGGCGGCGGCTGCCCAATAATGAACCTTCACTCT
GAGTACACCAACTCGTTCGAACAGTTCATCGATCGTG
TCATCTGGGAGAACTTCTACAAGCCCATCGTTTACAT
CGGTACCGACTCTGCTGAAGAGGAGGAAATTCTCCTT
GAAGTTTCCCTGGTGTTCAAAGTAAAGGAGTTTGCAC
CAGACGCACCTCTGTTCACTGGTCCGGCGTATTAA:
ATGGCAGACGTAGCAGGAACAAGTAACCGAGACTTTC SEQ ID NO: 4
GCGGACGCGAACAAAGACTATTCAATAGCGAACAATA
CAACTATAACAACAGCTTGAACGGAGAAGTGAGCGTG
TGGGTATACGCATACTACTCAGACGGGTCTGTACTCG
TAATCAACAAGAACTCGCAATACAAGGTTGGCATTTC
AGAGACATTCAAGGCACTTAAGGAATATCGCGAGGGA
CAACACAACGACTCTTACGATGAGTATGAAGTGAATC
AGAGCATCTACTATCCTAACGGCGGTGACGCTCGCAA
ATTCCATTCAAATGCTAAACCACGCGCGATCCAGATC
ATCTTCAGTCCTAGTGTGAATGTGCGTACTATCAAGA
TGGCTAAAGGCAACGCGGTATCCGTGCCCGATGAGTA
CCTACAGCGATCTCACCCATGGGAAGCGACCGGAATC
AAGTACCGCAAGATTAAGAGAGACGGGGAAATCGTTG
GTTACAGCCATTACTTTGAACTACCCCATGAATACAA
CTCCATCTCCCTAGCGGTAAGTGGTGTACATAAGAAC
CCATCATCATACAATGTCGGATCAGCACATAACGTAA
TGGACGTCTTCCAATCATGCGACTTGGCTCTCAGATT
CTGCAACCGCTACTGGGCCGAACTCGAATTGGTGAAC
CACTACATTTCGCCGAACGCCTACCCATACCTCGATA
TTAACAATCATAGCTATGGAGTAGCTCTGAGTAACCG
TCAGTGA:
ATGGTGAGCAAGCAGATCCTGAAGAACACCGGCCTGC SEQ ID NO: 6
AGGAGATCATGAGCTTCAAGGTGAACCTGGAGGGCGT
GGTGAACAACCACGTGTTCACCATGGAGGGCTGCGGC

AAGGGCAACATCCTGTTCGGCAACCAGTTGGTGCAGA
TCCGCGTGACCAAGGGCGCCCCCCTGCCCTTCGCCTT
CGACATCCTGAGCCCCGCCTTCCAGTACGGCAACCGC
ACCTTCACCAAGTACCCCGAGGACATCAGCGACTTCT
TCATCCAGAGCTTCCCCGCCGGCTTCGTGTACGAGCG
CACCCTGCGCTACGAGGACGGCGGCCTGGTGGAGATC
CGCAGCGACATCAACCTGATCGAGGAGATGTTCGTGT
ACCGCGTGGAGTACAAGGGCCGCAACTTCCCCAACGA
CGGCCCCGTGATGAAGAAGACCATCACCGGCCTGCAG
CCCAGCTTCGAGGTGGTGTACATGAACGACGGCGTGC
TGGTGGGCCAGGTGATCCTGGTGTACCGCCTGAACAG
CGGCAAGTTCTACAGCTGCCACATGCGCACCCTGATG
AAGAGCAAGGGCGTGGTGAAGGACTTCCCCGAGTACC
ACTTCATCCAGCACCGCCTGGAGAAGACCTACGTGGA
GGACGGCGGCTTCGTGGAGCAGCACGAGACCGCCATC
GCCCAGCTGACCAGCCTGGGCAAGCCCCTGGGCAGCC
TGCACGAGTGGGTGTAA:
ACCACCTCTGCGGGTGAGTCTGCGGACCCCGTGACTG SEQ ID NO: 8
CCACCGTCGAGAACTACGGTGGTGAGACACAAGTCCA
GAGGCGCCAGCACACGGACATTGCGTTCATATTGGAC
AGGTTCGTGAAAGTCAAGCCAAAGGAACAAGTTAATG
TGTTGGACCTGATGCAGATCCCTGCCCACACCTTGGT
AGGGGCGCTCCTGCGAACGGGCACCTACTACTTGTCT
GACCTGGAGCTGGCCGTCAAGCACGAAGGCGATCTCA
CCTGGGTCCCAAACGGCGCCCCTGAGACAGCACTGGA
CAACACTACCAACCCAACAGCTTACCACAAGGAACCC
CTCACACGGCTGGCGCTGCCTTACACGGCTCCACACC
GTGTCTTAGCGACCGTCTACAACGGGAGCAGTAAGTA
CGGTGACACCAGCACTAACAACGTGAGAGGTGACCTT
CAAGTGTTAGCTCAGAAGGCAGAAAGAACTCTGCCTA
CCTCCTTCAACTTCGGTGCCATCAAGGCAACTCGTGT
TACTGAACTACTCTACAGAATGAAGAGAGCCGAGACA
TACTGTCCCAGGCCCCTTCTCGCCATTCAACCGAGTG
ACGCTAGACACAAGCAGAGGATTGTGGCACCCGCAAA
ACAG:

A nucleic acid refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones, e.g., as these occur in a DNA library such as a cDNA or genomic DNA library. The nucleic acid described above can be used to express a fusion protein of this invention. For this purpose, one can operatively link the nucleic acid to suitable regulatory sequences to generate an expression vector.

A vector refers to a nucleic acid molecule capable of transporting another nucleic acid to which it has been linked. The vector can be capable of autonomous replication or integrate into a host DNA. Examples of the vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. A "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like.

The expression vector can be introduced into host cells to produce a fusion protein of this invention. Also within the scope of this invention is a host cell that contains the above-described nucleic acid. Examples include *E. coli* cells, insect cells (e.g., using baculovirus expression vectors), yeast cells, plant cells, or mammalian cells. See, e.g., Goeddel, (1990) Gene Expression Technology: Methods in Enzymology 185, Academic Press, San Diego, Calif. To produce a fusion protein of this invention, one can culture a host cell in a medium under conditions permitting expression of the protein encoded by a nucleic acid of this invention, and isolate the protein from the cultured cell or the medium of the cell. Preferably, the host cell is cultured in the absence of a wild type polyhedrin to produce the fusion protein that is contained in an occlusion body. The presence of the fusion protein in an occlusion body allows one to prepare the protein from the host cell by simply separating the occlusion body from the host cell.

Alternatively, the nucleic acid of this invention can be transcribed and translated in vitro, for example, using T7 promoter regulatory sequences and T7 polymerase.

The above-mentioned vector can be also used to make a recombinant virus, e.g., a recombinant baculovirus, as described below in Examples 2 and 4. The virus contains the nucleic acid encoding the fusion protein of this invention and can therefore be used to infect suitable host cells to express the fusion protein, thereby including a fused foreign polypeptide in an occlusion body.

Also within the scope of this invention is a recombinant occlusion body that contains the above-described fusion protein. This occlusion body can be free of a wild type polyhedrin of a virus. Preferably, it is also free of a particle of the virus, such as a CPV virion. In one embodiment, the polyhedrin sequence contains SEQ ID NO: 2. To prepare such a recombinant occlusion body, one can introduce the above-described recombinant virus into a host cell and culture the host cell to produce occlusion bodies.

This invention also features a composition containing the above-described recombinant occlusion body and a pharmaceutical acceptable carrier. One can use this composition to produce antibodies in a subject that recognize the foreign polypeptide.

The details of one or more embodiments of the invention are set forth in the accompanying drawings and the description below. Other features, objects, and advantages of the invention will be apparent from the description and from the claims.

DETAILED DESCRIPTION

This invention relates to a novel baculovirus expression system and a method for efficient isolation of engineered protein. The system is based, at least in part, on a fusion protein containing a viral polyhedrin sequence and a foreign polypeptide sequences. The fusion protein can form occlusion bodies in a host cell in the absence of a wild type polyhedrin, and be easily isolated from the cell.

The above-mentioned viral polyhedrin sequence can be that of any virus that form occlusion bodies in host cells (e.g., baculovirus, CPV, and spheroidin of the entomopox virus) or its functional equivalents. A "functional equivalent" refers to a polypeptide derived from a viral polyhedrin, e.g., fusion proteins or proteins having one or more point mutations, insertions, deletions, truncations, or combination thereof. It retains substantially the activity of the polyhedrin, i.e., the ability to form occlusion bodies in host cells. An exemplary polyhedrin contains SEQ ID NO: 1 or 2, or its fragment. The polyhedrin should be long enough, e.g., at least 70, 80, 100, 150, or 200, amino acids in length so as to be able to form occlusion bodies.

The foreign protein sequence can be that of any polypeptide of interest. For example, it can be a therapeutic polypeptide, such as a vaccine, an antibody chain, a biologically active peptide, a cytokine or its receptors, a growth factor or its receptor, and an enzyme. One can obtain nucleotide sequences encoding these polypeptides from various public databases, e.g., GenBank and the Kabat database (Ramirez-Benitez Mdel et al., Biosystems. 2001 61:125-31).

Once obtained, a foreign nucleotide sequence can be fused to that encoding a viral polyhedrin by standard recombinant technology. Preferably, the foreign nucleotide is fused in frame to the 3' end of the sequence encoding the viral polyhedrin to make a fusion gene. After making a fusion gene, one can operatively link it into an expression vector, which includes one or more regulatory sequences such as promoters. The baculovirus polyhedrin promoter is the most frequently used promoter for foreign gene expression.

To produce the above-described fusion protein in host cells, one can use standard baculovirus expression technology. See, e.g., Pfeifer et al., 1997, Gene 188:183-190; and Clem et al., 1994, J. Virol. 68:6759-6762. Suitable host cells may vary depending on the designs of systems or consideration of specificity. Examples of suitable host cells include, but are not limited to, the cells derived from species ranging from insects to vertebrates. Preferred host cells are insect-derived cells and mammalian cells. Examples of the insect-derived cells include Sf21, cells, Kc cells, and C6/36 cells. Upon expression, a plurality of the fusion proteins form recombinant occlusion bodies (i.e., occlusion body-like particles) in host cells.

It is known that at the very late stage of baculovirus infection, abundant polyhedrin proteins are produced and form occlusion bodies in the nucleus, a visible marker of baculovirus infection (Katsuma et al., 2000, Virus Genes 21, 233-240; Vialard et al., 1995, Introduction to the molecular biology of baculoviruses. Methods in Molecular biology. In Baculovirus Expression Protocols, Edited by C. D. Richardson. Totowa, N.J. Humana Press Inc.). A recombinant occlusion body of this invention is formed without co-infection of wild type baculovirus or the presence of wild type baculovirus polyhedrin. Besides baculovirus polyhedrin, other viral polyhedrin, e.g., CVP polyhedrin, can also occlude foreign protein into recombinant occlusion bodies in the absence any wild type polyhedrin. This is unexpected as Je et al., 2003, Biotechniques 34, 81-87 has reported that occlusion of foreign protein requires coexpression of wild type native polyhedrin. Such co-expression has several disadvantages as compared with the present invention. First, providing wild type polyhedrin requires extra work and increases difficulty for cloning. Second, wild type polyhedrin significantly dilutes the concentration of foreign protein. Third, in order to provide two sets of proteins, i.e. wild type polyhedrin and foreign protein, dual promoters or different viruses are needed. Because of the differences in promoter strengths and competition of two closely adjacent promoters, it is difficult to control the quality of the engineered foreign protein and the ratio of the wild type polyhedrin to the foreign protein. For these reasons, the expression described therein is superior to the co-expression system.

Like wild-type occlusion bodies, recombinant occlusion bodies of this invention can have sizes ranging from 0.5 to 15 um in diameter, with the predominant sizes ranging around 1.5 to 2.0 um in diameter (Adams et al., 1991, Chapter 6. Baculoviridae. Muclear polyhedrosis viruses. In Atlas of Invertebrate viruses, pp. 87-226. Edited by J. R. a. B. Adams. Boca Raton, Ann Arbor, Boston, and London: J. R. CRC Press.). Their shapes are slightly heterogenous: they may be cuboidal, tetrahedral, dodecahedral, or irregular. They retain in host cells long after cell lysis and do not disperse until a fully degradation of the cells. Accordingly, any engineered non-secretory proteins stay in the cells until a final complete cell lysis, thereby avoiding protein loss often seen in conventional protein expression systems.

The just-described recombinant occlusion bodies are water insoluble and readily to precipitate from a solution. Thus they are easy to purify. As described in Example 1 below, one can purify them from host cells simply by low speed centrifugation. Purified occlusion bodies can be further dissolved under a weak alkaline condition (O'Really et al., 1994, Baculovirus Expression Vectors: A Laboratory Manual. New York: Oxford University Press) to release engineered proteins. The engineered proteins can be further treated by various art-recognized methods, e.g., by enzymatic digestion, to remove the fusion partner and to obtain the recombinant foreign polypeptide.

The recombinant occlusion body-based expression system has a number of advantages over conventional baculovirus systems. First, the yield of engineered protein is high. Second, there is no loss of the engineered protein. Third, the fusion proteins form occlusion bodies that hold the proteins tightly through out the entire cell culture time. Thus, the timing for protein harvesting is not critical and it is easy to purify the engineered protein. As mentioned above, CPV polyhedrins also occlude fused foreign proteins into recombinant occlusion bodies. The use of CPV polyhedrin has its advantages. For example, fusion proteins are brought to the cytoplasmic region, instead of the nucleic region. As a result, the recombinant occlusion bodies are free of entangling cellular DNA upon purification. Furthermore, baculovirus virions are generated in the nucleic region. Thus, the CPV polyhedrin-containing recombinant occlusion bodies are free of baculovirus virions, thereby avoiding contamination.

This system combines the advantages of column-free, timesaving, and high-yields for protein harvesting. Accordingly, it is an excellent tool for expressing and preparing soluble, insoluble, low-level, toxic, or hard-to-purified foreign proteins.

In addition, the structure and function of foreign proteins, e.g., GFP and FMDV VP1, can be maintained in the aggregated crystal-like recombinant occlusion bodies. See the Examples below. In particular, the proteins maintain their antigenicity and can be well recognized by the immune system of animals even buried in the occlusion bodies. Accordingly, the occlusion body can be administered to animals (e.g., mice, rats, rabbits, goats, sheep, horses, and humans) to produce antibodies that recognize the foreign protein.

Thus, within the scope of this invention is an immunogneic or antigenic composition that contains a pharmaceutically acceptable carrier and an effective amount of a recombinant occlusion body of this invention. The carriers used in the composition are selected on the basis of the mode and route of administration, and standard pharmaceutical practice. Suitable pharmaceutical carriers and diluents, as well as pharmaceutical necessities for their use, are described in Remington's Pharmaceutical Sciences. An adjuvant, e.g., a cholera toxin, *Escherichia coli* heat-labile enterotoxin (LT), liposome, or immune-stimulating complex (ISCOM), can also be included in the composition, if necessary. Various adjuvants that can be used to increase the immunological response depend on the host species and include Freund's adjuvant (complete and incomplete), mineral gels such as aluminum hydroxide, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*.

The amount of a composition administered will depend, for example, on the particular peptide antigen in the foreign polypeptide, whether an adjuvant is co-administered with the antigen, the type of adjuvant co-administered, the mode and frequency of administration, and the desired effect (e.g., protection or treatment), as can be determined by one skilled in the art. In general, the recombinant occlusion body is administered in amounts ranging between 1 μg and 100 mg per adult human dose. If adjuvants are co-administered, amounts ranging between 1 ng and 1 mg per adult human dose can generally be used. Administration is repeated as necessary, as can be determined by one skilled in the art. For example, a priming dose can be given to a subject followed by three booster doses at weekly intervals. A booster shot can be given at 8 to 12 weeks after the first administration, and a second booster can be given at 16 to 20 weeks, using the same formulation. Sera can be taken from the subject for testing the immune response or antibody production elicited by the composition against the foreign polypeptide or polyhedrin. Methods of assaying antibodies against a specific antigen are well known in the art. Additional boosters can be given as needed. By varying the amount of recombinant occlusion body and frequency of administration, the protocol can be optimized for eliciting a maximal production of the antibodies.

The examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

In this example, baculovirus polyhedrin was used to bring foreign proteins into occlusion body-like particles for easy purification.

Oligonucleotides 5'-TC<u>CCCGGG</u>ATCTGATCATGG-3' (SEQ ID NO: 9) and 5'-CGC <u>AGATCT</u>AGT-GAACAGAGGTGC-3' (SEQ ID NO: 10) were used to amplify a region between nucleotide (nt) 4,520 to 5,257 of the AcMNPV genome (Ayres et al., 1994, Virology 202, 586-605, GenBank Accession No: NC_001623.). This region contains the polyhedrin promoter and gene. The oligonucleotides were designed to contain a SmaI site and a BglII site (both underlined). After PCR amplification, an 837-bp product was obtained, subjected to SmaI and BglII double digestion, and cloned into the EcoRV and BglII sites of pBacPAK8 (Clontech, Palo Alto, Calif.) to generate a transfer vector pBacPOL. The insertion was then confirmed by DNA sequencing. Subsequently, a 0.73-kb BamHI-EcoRI fragment containing the hrGFP gene was excised from the phrGFP-1 plasmid (Stratagene, La Jolla, Calif.) and inserted between the BglII and EcoRI sites of pBacPOL to generate a 7.0-kb transfer vector pABpPHG. In this vector, the hrGFP gene was fused downstream to the polyhedrin gene. This transfer vector was used to construct a recombinant virus vABpPHG for expressing a polyhedrin-hrGFP (PHG) fusion protein under the control of the very late polyhedrin promoter.

Two other oligonucleotides, 5'-AA<u>AGATCT</u>ACCACCTCTGCGGGTG-3' (SEQ ID NO: 11) (BglII site underlined) and 5'-G<u>GAATTC</u>AGAAGCTATTTTGCGGG-3' (SEQ ID NO: 12) (EcoRI site underlined), were used to amplify the vp1 gene from nt 2,840 to 3,478 of the foot and mouth disease virus (FMDV type O Taiwan) genome (GenBank Accession No. AF026168). The amplified 653-bp vp1 gene fragment was digested with BglII and EcoRI and then inserted into the BglII/EcoRI sites of pBacPOL to generate a 6.9-kb transfer vector pABpPVP1.

Both pABpPHG and pABpPVP1 were verified by DNA sequencing to confirm that the hrGFP gene and FMDV vp1 gene were precisely fused in frame to the C-terminus of polyhedrin gene. They were then used to infect host cells.

The transfer plasmids were co-transfected into $2\times10^5$ podoptera frugiperda IPLB-Sf21 (Sf21) cells on a 24-well plate at 26° C. with the linear viral DNA BaculoGold™ (PharMingen, San Diego, Calif.). Briefly, cells in each well were incubated with a transfection mixture containing 1.5 µg of DNA, 2 µl of Lipofectin® (Invitrogen, Carlsbad, Calif.) and 200 µl of serum-free TNM-FH medium following the protocol provided by manufacturer. After 8-14 hours of incubation, the transfection mixture was replaced by 300-µl of TNM-FH medium containing 8% heat-inactivated fetal bovine serum and cultured for 3-5 days. The recombinant viruses were isolated by the formation of occlusion body-like structures using end point dilution method (O'Reilly et al., 1994 Baculovirus Expression Vectors: A Laboratory Manual. New York: Oxford University Press). These recombinant viruses, as well as wild-type AcMNPV were propagated also using SF21 cells according to standard techniques.

The recombinant viruses were then used to infect SF21 cells. More specifically, the cells ($2\times10^7$) were incubated with the above-described recombinant viruses at a MOI of 5 while being gently rocked for 1 hour. At different times after infection, the cells were examined by fluorescence microscope (IX70, Olympus) under a ×20 objective lens. Upon excitation by 470/520 nm, the green fluorescence emitted at 505/530 nm was recorded by a digital camera system (DP50, Olympus). A confocal fluorescence microscope (LSM 510, Zeiss) was used for both higher magnification observation and optical section (in 0.2 µm depth) to study recombinant occlusion bodies.

It was found that green fluorescence was detectable at 2 dpi in the Sf21 cells infected with vABpPHG. At the same time, condensed green fluorescence spots began to be observable inside the nucleus. At 3 dpi, the number and the intensity of green fluorescent spots greatly increased. At 4 dpi, the recombinant occlusion bodies became more evident in both bright and fluorescence fields. This result suggests that vABpPHG alone could produce occlusion body-like structure without the co-infection of wild type virus. These recombinant occlusion bodies formed by the fusing protein PHG were slightly smaller than those formed by wild type polyhedrin.

It was also found that in Sf21 cells co-infected with vABpPHG and wild type virus AcMNPV, the size of recombinant occlusion bodies varied from cells to cells, and even crystals to crystals. Some of the recombinant occlusion bodies were larger than those generated by PHG along, suggesting that wild-type polyhedrin may participate in the formation of these recombinant occlusion bodies by PHG.

The above-described pABpPVP1 transfer plasmid was also infected into Sf21 cells to generate corresponding recombinant viruses. These viruses were then used to infect SF21 cells to produce fusion proteins of polyhedrin and FMDV VP1 protein (PVP1). The fusion protein was studied in the same manner described above to test whether it incorporated into the recombinant occlusion bodies. It was found that vABpPVP1 alone produced recombinant occlusion bodies in the absence of wild type virus. The recombinant occlusion bodies were observed in the infected cells and the sizes of these particles were about the same as that formed by PHG.

Since the PHG or PVP1 protein aggregated in recombinant occlusion bodies, high percentage recovery should be easily achieved. The expression levels of PHG were then determined by a time-course experiment. Briefly, $3\times10^5$ Sf21 cells were seeded in each well of a 6-wells plate and infected with vABpPHG at an MOI of 1. The cells were harvested at 3, 4, and 5 dpi and followed by PBS washing. The cell pellets were lysed and subjected to a SDS-PAGE analysis. It was found that a major band at 56 kDa matching the predicted molecular weight of PHG, and that PHG expression reached the highest level around 4 dpi.

The recombinant occlusion bodies generated in Sf21 cells infected by vABpPHG or AcMNPV were purified. More specifically, at 4 dpi, the infected cells were harvested by centrifugation at 2,000×g for 5 minutes at room temperature and then resuspended in 5 ml of 0.5% SDS-0.5 M NaCl to a concentration of $10^8$ cells/5 ml. The resuspension was gently shaken for 20 minutes at room temperature before being centrifuged at 5,000×g for 10 minutes. The pellets were resuspended in 1 ml of phosphate buffered saline (PBS, pH7.8) at 4° C. and then transferred to a fresh microcentrifuge tube. The majority of the pellet was recombinant occlusion bodies, which were confirmed by microscope at relatively a low magnification.

The purified recombinant occlusion bodies were then examined by confocal microscopy. It was found that PHG formed irregular recombinant occlusion bodies with sizes about 1.5 to 2.0 µm in diameter. The recombinant occlusion bodies were examined by optical section to confirm that PHG formed and incorporated into the recombinant occlusion bodies, rather than attached to the surface. Continuous sections showed that the green fluorescence was evenly distributed throughout the entire recombinant occlusion body. This result indicates that PHG was embedded in the recombinant occlusion bodies.

The purified recombinant occlusion bodies were also subjected to a SDS-PAGE/Coomassie brilliant blue staining. The results showed major protein products of 56, 29, and 57 kDa corresponding to PHG, AcMNPV polyhedrin, and PVP1 proteins, respectively. More importantly, it was shown that more than 95% purity of PVP1 or PHG could be achieved.

Gross protein yields from the infected cells and from recombinant occlusion bodies were then studied using recombinant virus vABpPVP1. The gross yield of PVP1 from total cell lysate was found to be 405 µg/ml. From purified recombinant occlusion bodies, a yield of 233 µg/ml was achieved. This is a 5 8% recovery from original 405 µg/ml of PVP1 fusion protein. To achieve an even higher purity for raising antibodies, the recombinant occlusion bodies were further purified through a 40% (w/w) sucrose cushion by a centrifugation of 100,000 g for 30 minutes.

EXAMPLE 2

In Example 1 above, it was shown that PHG emitted strong green fluorescence, suggesting that the fusion protein retained its structure and function in recombinant occlusion bodies. In this example, the above-described PHG and PVP1 fusion proteins were used to generate anti-sera that specifically recognize polyhedrin, PHG, and PVP1 in a group of mice.

More specifically, each mouse was immunized with 50 µg antigen mixed with Freund's complete adjuvant (Sigma, Saint Louis, Mo.) per injection per week for 3 weeks. Antigens used included PHG, PVP1, PHG-containing purified occlusion bodies, PVP1-containing purified occlusion bodies, and polyhedrin-only-containing purified occlusion bodies. Anti-PHG, anti-PVP1, and anti-polyhedrin antisera were then produced by standard techniques.

Immunoblot was conducted to exam the fusion proteins. Briefly, Sf21 cells mocked-infected and infected with vABpPHG, vABpPVP1, and wild type AcMNPV were prepared and harvested at 4 dpi in the manner described above. Total cellular lysates and purified proteins were subjected to 10% SDS-PAGE and transferred to membranes for Western analysis. The membranes were then blotted respectively by mouse anti-PHG, anti-PVP1, and anti-polyhedrin antisera, as well as anti-hrGFP antibodies. After washing by 1×PBS containing 0.1% triton X-100, blotted membranes were incubated with goat anti-mouse IgG HRP-conjugated secondary antibody for 1 hour and then visualized by the ECL detection system (Perkin-Elmer, Wellesley, Mass.).

It was found that PHG could be recognized by anti-hrGFP antibodies, as well as sera raised against polyhedrin, PHG, and PVP1. All fusion proteins (PVP1 and PHG) and polyhedrin were recognized by the antibody raised against polyhedrin.

Since the anti-PHG antiserum was induced by the fusion protein containing both hrGFP and polyhedrin, the raised antibodies should recognize both proteins. Indeed, it was found that antiserum raised against PHG recognized both polyhedrin and PHG. To confirm this deduction, the antiserum was 1,500× diluted and incubated with 5-µg purified AcMNPV polyhedra in a 3 ml solution at 37° C. for 2 hours to deplete anti-polyhedrin antibodies. The antiserum thus-depleted was used in immunoblot analysis in the same manner described above. It was found that the intensity of signal corresponding to polyhedrin reduced drastically. In contrast, the signal of PHG remained. This result indicates that undepleted antiserum contains antibodies against both proteins and that depleted antiserum contains antibodies against GFP. It also suggests that a protein fused to the polyhedrin retains its antigenicity after being incorporated into recombinant occlusion bodies.

EXAMPLE 3

In this example, early leakage of engineered proteins in cells infected by baculovirus was examined. Briefly, SF21 cells were infected with vABpPHG and vAbhRpX in the manner described above. Upon infection with vABpPHG and vAbhRpX, the cells expressed fused GFP and red fluorescence protein DsRed, respectively. It is known that the fused GFP stays in a cell even after cell lysis and that, on the contrary, DsRed is cytosolic-localized and leaks out upon cell lysis.

It was found that the hrGFP was brought to the nucleus of the host cells by the polyhedrin fusion partner and stayed there even after the cells were totally lysed at 7 dpi. The DsRed, not capable of forming recombinant occlusion bodies, was found in the cytosol before cell lysis (3 dpi). Afterwards, DsRed began to leak out from some cells. More significant leakage of the DsRed was observed at 4 and 5 dpi, a stage most frequently used for harvesting engineered protein. At 7 dpi, all DsRed leaked out of the cells. In contrast, the fused hrGFP stayed in the cell long after all infected cells lyzed (7 dpi) without detectable loss. These results suggest that the polyhedrin fusion partner retains an engineered protein in host cells, and allows one to purify it at a high recovery rate at all stages after viral infection.

EXAMPLE 4

In this example, cytoplasmic polyhedrosis virus (CPV) polyhedrin was used to carry foreign proteins into the recombinant occlusion bodies for easy purification. CPV, a reovirus, has a RNA genome and forms occlusion bodies in the cytoplasmic region.

A pag promoter was PCR synthesized using primer pairs: Forward 5'-ATAGATATC-TACTCATCGACCAAT GGCGTCGCTCGGTTCTTATCGCAACAGAGTGG GGGCCATCCG CACTATAAAAAGCCGAGAC (SEQ ID NO: 13) and Reverse5'-ATAGTCAACTGCCAA GCTTG-GTATGAACACGACTCGAATCAGACTGATGGT GTTCGTCACCAGTCTCGGCTTTTTATAGTGCGG (SEQ ID NO: 14) (Chao et al., 1998 J. Virol. 72, 2233-2245.). The two primers contained EcoRV and HindII restriction sites (underlined). A DsRed2 coding region was amplified from pDsRed2 (Clontech, Palo Alto, Calif.) using primers 5'-ATA<u>GTTGAC</u>GGTCGCCACCATGGCC (SEQ ID NO: 15) and 5'-ATAGTCAAC <u>GATATC</u>TACAGGAACAGGTGGTGG(SEQ ID NO: 16) (EcoRV and HindII restriction sites underlined). The two fragments were ligated at the HindII sites and then inserted into pBacPAK8 at EcoRV site opposite to the transcriptional direction of polyhedrin promoter. The resulted plasmid was named pABpagR2pX.

To generate hrGFP- or EGFP-fusion proteins under the control of polyhedrin promoter, the full-length polyhedrin gene of *Bombyx mori* cytoplasmic polyhedrosis virus (BmCP) was synthesized according to the sequence of NCBI GI 332496 from 42 to 788 (Arella et al., 1998, J. Virol. 62, 211-217). Restriction sites XhoI and EcoRI sites were added immediately before the translation start codon and after the stop codon, respectively to facilitate inserting the polyhedrin gene into the multiple cloning sites of pABpagR2pX down streaming the polyhedrin promoter of AcMNPV. The result plasmid was named pABpagR2pBmCP. Then the hrGFP-coding region was PCR amplified by 5'-GCGGATCCAC-CATGGTGAGCAAGCAGA (SEQ ID NO: 17) and 5'-AATCTCGAGCACCCAC TCGTGCAGGCT (SEQ ID NO: 18) from phrGFP-1, in which the later primer replaced the stop codon to XhoI site. Similarly, the EGFP coding region was PCR amplified by 5'-TAGGATCCGCCAC-CATGGTGAGCAA (SEQ ID NO: 19) and 5'-AATCTCGA GCTTGTACAGCTCGTCCAT (SEQ ID NO: 20) from pEGFP-C1 (Clontech, Palo Alto, Calif.) and the stop coden was substituted by XhoI site. The amplified fragments were enzyme digested and inserted into the pABpagR2pBmCP vector at BamHI and XhoI site to obtain pABpagR2pHRCP and pABpagR2 pEGCP, respectively.

The vectors described above were transfected into Sf21 cells to generate recombinant viruses by standard techniques. Cells infected with the recombinant viruses were studied in the manner described above. It was found that the cells contained distinct recombinant occlusion bodies. Confocal optical section study further confirmed that these particles were located in the cytoplasmic region of the cells. Since baculovirus virions are only produced in the nucleus, this result suggests that these recombinant occlusion bodies do not include any virions.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A fusion protein comprising
   a polyhedrin sequence of a virus, the polyhedrin sequence being SEQ ID NO:2 or a fragment thereof, at least 70 amino acids in length, that can form occlusion bodies in a host cell, and a foreign polypeptide sequence that is at least 100 amino acids in length, wherein a plurality of the fusion proteins, in the absence of a wild type polyhedrin of a virus, form occlusion bodies in a host cell.

2. The fusion protein of claim 1, wherein the foreign polypeptide sequence is 100-500 amino acids in length.

3. The fusion protein of claim 1, wherein the foreign polypeptide contains a GFP or VP1 protein sequence.

4. The fusion protein of claim 3, wherein the foreign polypeptide contains SEQ ID NO: 5 or 7.

5. A nucleic acid encoding the fusion protein of claim 1.

6. The nucleic acid of claim 5, wherein the nucleic acid contains SEQ ID NO: 6 or 8.

7. A vector comprising the nucleic acid of claim 5.

8. A host cell comprising the nucleic acid of claim 5.

9. The host cell of claim 8, wherein the host cell is an *E. coli*, yeast, insect, or mammalian cell.

10. The host cell of claim 9, wherein the host cell is an insect cell.

11. A recombinant virus comprising the nucleic acid of claim 5.

12. A recombinant occlusion body comprising the fusion protein of claim 1.

13. The occlusion body of claim 12, wherein the occlusion body is free of a wild type polyhedrin of a virus.

14. The occlusion body of claim 13, wherein the occlusion body is free of a particle of a virus.

15. The occlusion body of claim 12, wherein the occlusion body is free of a particle of a virus.

16. A method of preparing an occlusion body, comprising:
    introducing a recombinant virus of claim 11 into a host cell; and
    culturing the host cell to produce an occlusion body, wherein the occlusion body is free of a wild type polyhedrin.

17. A method of preparing a foreign polypeptide from a host cell, the method comprising
    culturing the host cell of claim 8 for expressing the foreign polypeptide, and isolating the polypeptide.

18. The method of claim 17, wherein the host cell is cultured in the absence of a wild type polyhedrin to produce the foreign polypeptide that is contained in an occlusion body.

19. A composition comprising the recombinant occlusion body of claim 12 and a pharmaceutical acceptable carrier, wherein the fusion protein is antigenic.

20. A method of producing antibodies that recognize a foreign polypeptide in a subject, the method comprising administering to the subject the recombinant occlusion body of claim 12.

21. The fusion protein of claim 1, wherein the fragment is at least 150 amino acids in length.

22. The fusion protein of claim 1, wherein the fragment is at least 200 amino acids in length.

23. A fusion protein comprising
    a polyhedrin sequence of a virus, the polyhedrin sequence being SEQ ID NO: 2 and
    a foreign polypeptide sequence that is at least 10 amino acids in length, wherein a plurality of the fusion proteins, in the absence of a wild type polyhedrin of a virus, form occlusion bodies in a host cell.

24. A nucleic acid encoding the fusion protein of claim 23.

25. The fusion protein of claim 23, wherein the foreign polypeptide sequence is 100-500 amino acids in length.

26. A nucleic acid encoding the fusion protein of claim 25.

27. A vector comprising the nucleic acid of claim 26.

28. A host cell comprising the nucleic acid of claim 27.

* * * * *

SEQUENCE LISTING

<160> NUMBER OF SEQ ID NOS: 20

<210> SEQ ID NO 1
<211> LENGTH: 245
<212> TYPE: PRT
<213> ORGANISM: Autographa californica multicapsid nucleopolyhedrs

<400> SEQUENCE: 1

Met Pro Asp Tyr Ser Tyr Arg Pro Thr Ile Gly Arg Thr Tyr Val Tyr
1               5                   10                  15

Asp Asn Lys Tyr Tyr Lys Asn Leu Gly Ala Val Ile Lys Asn Ala Lys
            20                  25                  30

Arg Lys Lys His Phe Ala Glu His Glu Ile Glu Ala Thr Leu Asp
        35                  40                  45

Pro Leu Asp Asn Tyr Leu Val Ala Glu Asp Pro Phe Leu Gly Pro Gly
    50                  55                  60

Lys Asn Gln Lys Leu Thr Leu Phe Lys Glu Ile Arg Asn Val Lys Pro
65                  70                  75                  80

Asp Thr Met Lys Leu Val Val Gly Trp Lys Gly Lys Glu Phe Tyr Arg
                85                  90                  95

Glu Thr Trp Thr Arg Phe Met Glu Asp Ser Phe Pro Ile Val Asn Asp
            100                 105                 110

Gln Glu Val Met Asp Val Phe Leu Val Val Asn Met Arg Pro Thr Arg
        115                 120                 125

Pro Asn Arg Cys Tyr Lys Phe Leu Ala Gln His Ala Leu Arg Cys Asp
    130                 135                 140

```
Pro Asp Tyr Val Pro His Asp Val Ile Arg Ile Val Glu Pro Ser Trp
145                 150                 155                 160

Val Gly Ser Asn Asn Glu Tyr Arg Ile Ser Leu Ala Lys Lys Gly Gly
                165                 170                 175

Gly Cys Pro Ile Met Asn Leu His Ser Glu Tyr Thr Asn Ser Phe Glu
            180                 185                 190

Gln Phe Ile Asp Arg Val Ile Trp Glu Asn Phe Tyr Lys Pro Ile Val
        195                 200                 205

Tyr Ile Gly Thr Asp Ser Ala Glu Glu Glu Ile Leu Leu Glu Val
    210                 215                 220

Ser Leu Val Phe Lys Val Lys Glu Phe Ala Pro Asp Ala Pro Leu Phe
225                 230                 235                 240

Thr Gly Pro Ala Tyr
                245

<210> SEQ ID NO 2
<211> LENGTH: 248
<212> TYPE: PRT
<213> ORGANISM: Cytoplasmic polyhedrosis virus

<400> SEQUENCE: 2

Met Ala Asp Val Ala Gly Thr Ser Asn Arg Asp Phe Arg Gly Arg Glu
1               5                   10                  15

Gln Arg Leu Phe Asn Ser Glu Gln Tyr Asn Tyr Asn Asn Ser Leu Asn
            20                  25                  30

Gly Glu Val Ser Val Trp Val Tyr Ala Tyr Tyr Ser Asp Gly Ser Val
        35                  40                  45

Leu Val Ile Asn Lys Asn Ser Gln Tyr Lys Val Gly Ile Ser Glu Thr
    50                  55                  60

Phe Lys Ala Leu Lys Glu Tyr Arg Glu Gly Gln His Asn Asp Ser Tyr
65                  70                  75                  80

Asp Glu Tyr Glu Val Asn Gln Ser Ile Tyr Tyr Pro Asn Gly Gly Asp
                85                  90                  95

Ala Arg Lys Phe His Ser Asn Ala Lys Pro Arg Ala Ile Gln Ile Ile
            100                 105                 110

Phe Ser Pro Ser Val Asn Val Arg Thr Ile Lys Met Ala Lys Gly Asn
        115                 120                 125

Ala Val Ser Val Pro Asp Glu Tyr Leu Gln Arg Ser His Pro Trp Glu
130                 135                 140

Ala Thr Gly Ile Lys Tyr Arg Lys Ile Lys Arg Asp Gly Glu Ile Val
145                 150                 155                 160

Gly Tyr Ser His Tyr Phe Glu Leu Pro His Glu Tyr Asn Ser Ile Ser
                165                 170                 175

Leu Ala Val Ser Gly Val His Lys Asn Pro Ser Ser Tyr Asn Val Gly
            180                 185                 190

Ser Ala His Asn Val Met Asp Val Phe Gln Ser Cys Asp Leu Ala Leu
        195                 200                 205

Arg Phe Cys Asn Arg Tyr Trp Ala Glu Leu Glu Leu Val Asn His Tyr
210                 215                 220

Ile Ser Pro Asn Ala Tyr Pro Tyr Leu Asp Ile Asn Asn His Ser Tyr
225                 230                 235                 240

Gly Val Ala Leu Ser Asn Arg Gln
                245

<210> SEQ ID NO 3
```

-continued

```
<211> LENGTH: 738
<212> TYPE: DNA
<213> ORGANISM: Autographa californica multicapsid nucleopolyhedrs

<400> SEQUENCE: 3
atgccggatt attcataccg tcccaccatc gggcgtacct acgtgtacga caacaagtac      60
tacaaaaatt taggtgccgt tatcaagaac gctaagcgca agaagcactt cgccgaacat     120
gagatcgaag aggctaccct cgaccccta gacaactacc tagtggctga ggatcctttc      180
ctgggacccg gcaagaacca aaaactcact ctcttcaagg aaatccgtaa tgttaaaccc     240
gacacgatga agcttgtcgt tggatggaaa ggaaaagagt tctacaggga aacttggacc     300
cgcttcatgg aagacagctt ccccattgtt aacgaccaag aagtgatgga tgttttcctt     360
gttgtcaaca tgcgtcccac tagacccaac cgttgttaca aattcctggc caacacgct      420 ctgcgttgcg accccgacta tgtacctcat gacgtgatta ggatcgtcga gccttcatgg     480
gtgggcagca caacgagta ccgcatcagc ctggctaaga agggcggcgg ctgcccaata     540
atgaaccttc actctgagta caccaactcg ttcgaacagt tcatcgatcg tgtcatctgg     600
gagaacttct acaagcccat cgtttacatc ggtaccgact ctgctgaaga ggaggaaatt     660
ctccttgaag tttccctggt gttcaaagta aaggagtttg caccagacgc acctctgttc     720
actggtccgg cgtattaa                                                   738

<210> SEQ ID NO 4
<211> LENGTH: 747
<212> TYPE: DNA
<213> ORGANISM: Cytoplasmic polyhedrosis virus

<400> SEQUENCE: 4
atggcagacg tagcaggaac aagtaaccga gactttcgcg gacgcgaaca aagactattc      60
aatagcgaac aatacaacta taacaacagc ttgaacggag aagtgagcgt gtgggtatac     120
gcatactact cagacgggtc tgtactcgta atcaacaaga actcgcaata caaggttggc     180
atttcagaga cattcaaggc acttaaggaa tatcgcgagg acaacacaa cgactcttac      240 gatgagtatg aagtgaatca gagcatctac tatcctaacg gcggtgacgc tcgcaaattc     300
cattcaaatg ctaaaccacg cgcgatccag atcatcttca gtcctagtgt gaatgtgcgt     360
actatcaaga tggctaaagg caacgcggta tccgtgcccg atgagtacct acagcgatct     420
cacccatggg aagcgaccgg aatcaagtac cgcaagatta agagagacgg ggaaatcgtt     480
ggttacagcc attactttga actaccccat gaatacaact ccatctccct agcggtaagt     540
ggtgtacata gaacccatc atcatacaat gtcggatcag cacataacgt aatggacgtc     600
ttccaatcat gcgacttggc tctcagattc tgcaaccgct actgggccga actcgaattg     660
gtgaaccact acatttcgcc gaacgcctac ccatacctcg atattaacaa tcatagctat     720
ggagtagctc tgagtaaccg tcagtga                                        747

<210> SEQ ID NO 5
<211> LENGTH: 239
<212> TYPE: PRT
<213> ORGANISM: Foot and mouth disease virus

<400> SEQUENCE: 5

Met Val Ser Lys Gln Ile Leu Lys Asn Thr Gly Leu Gln Glu Ile Met
 1               5                  10                  15

Ser Phe Lys Val Asn Leu Glu Gly Val Val Asn Asn His Val Phe Thr
             20                  25                  30
```

```
Met Glu Gly Cys Gly Lys Gly Asn Ile Leu Phe Gly Asn Gln Leu Val
             35                  40                  45
Gln Ile Arg Val Thr Lys Gly Ala Pro Leu Pro Phe Ala Phe Asp Ile
         50                  55                  60
Leu Ser Pro Ala Phe Gln Tyr Gly Asn Arg Thr Phe Thr Lys Tyr Pro
65                  70                  75                  80
Glu Asp Ile Ser Asp Phe Phe Ile Gln Ser Phe Pro Ala Gly Phe Val
                 85                  90                  95
Tyr Glu Arg Thr Leu Arg Tyr Glu Asp Gly Leu Val Glu Ile Arg
                 100                 105                 110
Ser Asp Ile Asn Leu Ile Glu Glu Met Phe Val Tyr Arg Val Glu Tyr
                 115                 120                 125
Lys Gly Arg Asn Phe Pro Asn Asp Gly Pro Val Met Lys Lys Thr Ile
                 130                 135                 140
Thr Gly Leu Gln Pro Ser Phe Glu Val Val Tyr Met Asn Asp Gly Val
145                 150                 155                 160
Leu Val Gly Gln Val Ile Leu Val Tyr Arg Leu Asn Ser Gly Lys Phe
                 165                 170                 175
Tyr Ser Cys His Met Arg Thr Leu Met Lys Ser Lys Gly Val Val Lys
                 180                 185                 190
Asp Phe Pro Glu Tyr His Phe Ile Gln His Arg Leu Glu Lys Thr Tyr
                 195                 200                 205
Val Glu Asp Gly Gly Phe Val Glu Gln His Glu Thr Ala Ile Ala Gln
                 210                 215                 220
Leu Thr Ser Leu Gly Lys Pro Leu Gly Ser Leu His Glu Trp Val
225                 230                 235

<210> SEQ ID NO 6
<211> LENGTH: 720
<212> TYPE: DNA
<213> ORGANISM: Foot and mouth disease virus

<400> SEQUENCE: 6
atggtgagca agcagatcct gaagaacacc ggcctgcagg agatcatgag cttcaaggtg      60
aacctggagg gcgtggtgaa caaccacgtg ttcaccatgg agggctgcgg caagggcaac     120
atcctgttcg gcaaccagtt ggtgcagatc cgcgtgacca agggcgcccc cctgcccttc     180
gccttcgaca tcctgagccc cgccttccag tacggcaacc gcaccttcac caagtacccc     240
gaggacatca gcgacttctt catccagagc ttccccgccg gcttcgtgta cgagcgcacc     300
ctgcgctacg aggacggcgg cctggtggag atccgcagcg acatcaacct gatcgaggag     360
atgttcgtgt accgcgtgga gtacaagggc cgcaacttcc ccaacgacgg ccccgtgatg     420
aagaagacca tcaccggcct gcagcccagc ttcgaggtgg tgtacatgaa cgacggcgtg     480
ctggtgggcc aggtgatcct ggtgtaccgc ctgaacagcg gcaagttcta cagctgccac     540
atgcgcaccc tgatgaagag caagggcgtg gtgaaggact tccccgagta ccacttcatc     600
cagcaccgcc tggagaagac ctacgtggag gacggcggct tcgtggagca gcacgagacc     660
gccatcgccc agctgaccag cctgggcaag cccctgggca gcctgcacga gtgggtgtaa     720

<210> SEQ ID NO 7
<211> LENGTH: 213
<212> TYPE: PRT
<213> ORGANISM: Foot and mouth disease virus

<400> SEQUENCE: 7
```

```
Thr Thr Ser Ala Gly Glu Ser Ala Asp Pro Val Thr Ala Thr Val Glu
  1               5                  10                 15

Asn Tyr Gly Gly Glu Thr Gln Val Gln Arg Arg Gln Asp Thr Asp Ile
             20                  25                  30

Ala Phe Ile Leu Asp Arg Phe Val Lys Val Lys Pro Lys Glu Gln Val
         35                  40                  45

Asn Val Leu Asp Leu Met Gln Ile Pro Ala His Thr Leu Val Gly Ala
     50                  55                  60

Leu Leu Arg Thr Ala Thr Tyr Tyr Phe Ser Asp Leu Glu Leu Ala Val
 65                 70                  75                  80

Lys His Glu Gly Asp Leu Thr Trp Val Pro Asn Gly Ala Pro Glu Thr
                 85                  90                  95

Ala Leu Asp Asn Thr Thr Asn Pro Thr Ala Tyr His Lys Glu Pro Leu
             100                 105                 110

Thr Arg Leu Ala Leu Pro Tyr Thr Ala Pro His Arg Val Leu Ala Thr
         115                 120                 125

Val Tyr Asn Gly Ser Ser Lys Tyr Gly Asp Thr Ser Thr Asn Asn Val
 130                135                 140

Arg Gly Asp Leu Gln Val Leu Ala Gln Lys Ala Glu Arg Thr Leu Pro
145                 150                 155                 160

Thr Ser Phe Asn Phe Gly Ala Ile Lys Ala Thr Arg Val Thr Glu Leu
             165                 170                 175

Leu Tyr Arg Met Lys Arg Ala Glu Thr Tyr Cys Pro Arg Pro Leu Leu
         180                 185                 190

Ala Ile Gln Pro Ser Asp Ala Arg His Lys Gln Arg Ile Val Ala Pro
         195                 200                 205

Ala Lys Gln Leu Leu
        210

<210> SEQ ID NO 8
<211> LENGTH: 633
<212> TYPE: DNA
<213> ORGANISM: Foot and mouth disease virus

<400> SEQUENCE: 8
accacctctg cgggtgagtc tgcggacccc gtgactgcca ccgtcgagaa ctacggtggt      60
gagacacaag tccagaggcg ccagcacacg gacattgcgt tcatattgga caggttcgtg     120
aaagtcaagc caaaggaaca agttaatgtg ttggacctga tgcagatccc tgcccacacc     180
ttggtagggg cgctcctgcg aacgggcacc tactacttgt ctgacctgga gctggccgtc     240
aagcacgaag gcgatctcac ctgggtccca acggcgccc tgagacagc actgacaac      300 actaccaacc caacagctta ccacaaggaa cccctcacac ggctggcgct gccttacacg     360
gctccacacc gtgtcttagc gaccgtctac aacgggagca gtaagtacgg tgacaccagc     420
actaacaacg tgagaggtga ccttcaagtg ttagctcaga aggcagaaag aactctgcct     480
acctccttca acttcggtgc catcaaggca actcgtgtta ctgaactact ctacagaatg     540
aagagagccg agacatactg tcccaggccc cttctcgcca ttcaaccgag tgacgctaga     600
cacaagcaga ggattgtggc acccgcaaaa cag                                  633

<210> SEQ ID NO 9
<211> LENGTH: 20
<212> TYPE: DNA
<213> ORGANISM: Artificial Sequence
<220> FEATURE:
```

<223> OTHER INFORMATION: Synthetically generated oligonucleotide

<400> SEQUENCE: 9
tccccgggat ctgatcatgg                                                    20

<210> SEQ ID NO 10
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 10
cgcagatcta gtgaacagag gtgc                                               24

<210> SEQ ID NO 11
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 11
aaagatctac cacctctgcg ggtg                                               24

<210> SEQ ID NO 12
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 12
ggaattcaga agctattttg cggg                                               24

<210> SEQ ID NO 13
<211> LENGTH: 85
<212> TYPE: DNA
<213> ORGANISM: Artificial Sequence
<220> FEATURE:
<223> OTHER INFORMATION: Primer

<400> SEQUENCE: 13
atagatatct actcatcgac caatggcgtc gctcggttct tatcgcaaca gagtgggggc        60
catccgcact ataaaaagcc gagac                                              85

<210> SEQ ID NO 14
<211> LENGTH: 84
<212> TYPE: DNA
<213> ORGANISM: Artificial Sequence
<220> FEATURE:
<223> OTHER INFORMATION: Primer

<400> SEQUENCE: 14
atagtcaact gccaagcttg gtatgaacac gactcgaatc agactgatgg tgttcgtcac        60
cagtctcggc tttttatagt gcgg                                               84

<210> SEQ ID NO 15
<211> LENGTH: 25
<212> TYPE: DNA
<213> ORGANISM: Artificial Sequence
<220> FEATURE:
<223> OTHER INFORMATION: Primer

<400> SEQUENCE: 15

```
atagttgacg gtcgccacca tggcc                                      25

<210> SEQ ID NO 16
<211> LENGTH: 33
<212> TYPE: DNA
<213> ORGANISM: Artificial Sequence
<220> FEATURE:
<223> OTHER INFORMATION: Primer

<400> SEQUENCE: 16
atagtcaacg atatctacag gaacaggtgg tgg                             33

<210> SEQ ID NO 17
<211> LENGTH: 27
<212> TYPE: DNA
<213> ORGANISM: Artificial Sequence
<220> FEATURE:
<223> OTHER INFORMATION: Primer

<400> SEQUENCE: 17
gcggatccac catggtgagc aagcaga                                    27

<210> SEQ ID NO 18
<211> LENGTH: 27
<212> TYPE: DNA
<213> ORGANISM: Artificial Sequence
<220> FEATURE:
<223> OTHER INFORMATION: Primer

<400> SEQUENCE: 18
aatctcgagc acccactcgt gcaggct                                    27

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19
taggatccgc caccatggtg agcaa                                      25

<210> SEQ ID NO 20
<211> LENGTH: 27
<212> TYPE: DNA
<213> ORGANISM: Artificial Sequence
<220> FEATURE:
<223> OTHER INFORMATION: Primer

<400> SEQUENCE: 20
aatctcgagc ttgtacagct cgtccat                                    27
```